United States Patent
Ni et al.

(10) Patent No.: US 10,822,593 B2
(45) Date of Patent: *Nov. 3, 2020

(54) ALCOHOL DEHYDROGENASE MUTANT AND APPLICATION THEREOF IN SYNTHESIS OF DIARYL CHIRAL ALCOHOLS

(71) Applicant: Jiangnan University, Wuxi (CN)

(72) Inventors: Ye Ni, Wuxi (CN); Jieyu Zhou, Wuxi (CN); Guochao Xu, Wuxi (CN); Yue Wang, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/521,656

(22) Filed: Jul. 25, 2019

(65) Prior Publication Data

US 2019/0345457 A1   Nov. 14, 2019

Related U.S. Application Data

(63) Continuation of application No. PCT/CN2018/094505, filed on Jul. 4, 2018.

(30) Foreign Application Priority Data

Feb. 12, 2018   (CN) .......................... 2018 1 01464637

(51) Int. Cl.
    *C12N 9/04*   (2006.01)
    *C12P 17/12*   (2006.01)

(52) U.S. Cl.
    CPC ............ *C12N 9/0006* (2013.01); *C12P 17/12* (2013.01); *C12Y 101/01001* (2013.01)

(58) Field of Classification Search
    CPC ...... C12N 9/0006; C12P 17/12; C12P 41/002; C12Y 101/01001
    See application file for complete search history.

(56) References Cited

FOREIGN PATENT DOCUMENTS

| CN | 102559520 A | 7/2012 |
|----|-------------|--------|
| CN | 105936895 A | 9/2016 |
| CN | 105936909 A | 9/2016 |
| CN | 106047985 A | 10/2016 |
| CN | 108359649 A | 8/2018 |
| CN | 108384765 A | 8/2018 |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Sadowski et al., Current Opinion in Structural Biology 19:357-362, 2009.*
Gordon et al., GenBank accession No. XP_022464010, Sep. 27, 2017.*
Zhou et al., GenBank accession No. 5ZEC_A, Jan. 3, 2019.*
Scannell et al., GenBank accession No. EDO15833, Aug. 17, 2007.*

* cited by examiner

*Primary Examiner* — Delia M Ramirez
(74) *Attorney, Agent, or Firm* — IPro, PLLC

(57) ABSTRACT

The present disclosure discloses an alcohol dehydrogenase mutant and application thereof in synthesis of diaryl chiral alcohols, and belongs to the technical field of bioengineering. The alcohol dehydrogenase mutant of the present disclosure has excellent catalytic activity and stereoselectivity, and may efficiently catalyze the preparation of a series of chiral diaryl alcohols in R- and S-configurations. By coupling alcohol dehydrogenase of the present disclosure to glucose dehydrogenase or formate dehydrogenase, the synthesis of chiral diaryl alcohol intermediates of various antihistamines may be achieved. Compared with the prior art, a method for preparing diaryl chiral alcohols through asymmetric catalytic reduction using the alcohol dehydrogenase of the present disclosure has the advantages of simple and convenient operation, high substrate concentration, complete reaction and high product purity, and has great industrial application prospects.

2 Claims, 3 Drawing Sheets

Specification includes a Sequence Listing.

SEQUENCE LISTING

<160> NUMBER OF SEQ ID NOS: 12

<210> SEQ ID NO 1
<211> LENGTH: 1029
<212> TYPE: DNA
<213> ORGANISM: Artificial Sequence
<220> FEATURE:
<223> OTHER INFORMATION: Synthetic DNA

<400> SEQUENCE: 1

```
atgagcgtat taattagtgg tgcttctgga tacattgcca aacatatcgt cagagttctt      60
ttggaacaaa attacaaagt aattggtact gttagaagtc aagacaaagc tgataagtta     120
ttgaaacaat ataataatcc taatttgtct tatgaaattg tacctgaaat agcaaactta     180
gatgcttttg atgacatttt taagaaacat ggtaaggaaa taaatatgt cattcatgca      240
gcttcaccag tgaacttcgg cgcaaaagat ttggaaaaag atttagttat tcctgccatt     300
aatggtacca agaatatgtt cgaagctatt aaaaagtatg ccccagatac tgtcgaacgt     360
gttgtaatga ctgcttctta tgcttcaatt atgaccccac atagacaaaa tgatccaact     420
ttaactttag atgaagaaac ttggaatcca gtaactgaag aaaatgctta tgaaaatgtc     480
ttcactgctt attgtgcttc aaaaactttt gctgaaaagg aagcttggaa gttcgttaaa     540
gaaaatagtg atgctgttaa gtttaaacta accactatcc acccatcctt cgttttcgga    600
cctcagaact tgatgaaga cgtcactaag aaactaaatg aaacttgtga attatcaat      660
ggtttattac atgctccatt tgacaccaaa gtcgaaaaga ctcacttcag tcaattcatt     720
gatgttcgtg atgtcgccaa aactcacgtt ttgggtttcc aaaaagatga attaatcaac     780
caaagattgt tattatgtaa cggcgccttc tctcaacaag atattgttaa tgtatttaat     840
gaagatttcc cagagttaaa aggccaattc ccaccagaag ataaggacac cgatttaaac     900
aaaggtgtaa caggttgtaa aattgataat gaaaagacta aaaaattatt agcatttgaa     960
tttactcctt tccataaaac aattcatgac actgtctatc aaattttaca taagaaggt    1020
agagtttaa                                                            1029
```

<210> SEQ ID NO 2
<211> LENGTH: 342
<212> TYPE: PRT
<213> ORGANISM: Artificial Sequence
<220> FEATURE:
<223> OTHER INFORMATION: Protein translated from synthetic DNA

<400> SEQUENCE: 2

```
Met Ser Val Leu Ile Ser Gly Ala Ser Gly Tyr Ile Ala Lys His Ile
1               5                   10                  15

Val Arg Val Leu Leu Glu Gln Asn Tyr Lys Val Ile Gly Thr Val Arg
            20                  25                  30

Ser Gln Asp Lys Ala Asp Lys Leu Leu Lys Gln Tyr Asn Asn Pro Asn
        35                  40                  45

Leu Ser Tyr Glu Ile Val Pro Glu Ile Ala Asn Leu Asp Ala Phe Asp
    50                  55                  60

Asp Ile Phe Lys Lys His Gly Lys Glu Ile Lys Tyr Val Ile His Ala
65                  70                  75                  80

Ala Ser Pro Val Asn Phe Gly Ala Lys Asp Leu Glu Lys Asp Leu Val
                85                  90                  95

Ile Pro Ala Ile Asn Gly Thr Lys Asn Met Phe Glu Ala Ile Lys Lys
            100                 105                 110
```

```
Tyr Ala Pro Asp Thr Val Glu Arg Val Val Met Thr Ala Ser Tyr Ala
            115                 120                 125

Ser Ile Met Thr Pro His Arg Gln Asn Asp Pro Thr Leu Thr Leu Asp
    130                 135                 140

Glu Glu Thr Trp Asn Pro Val Thr Glu Asn Ala Tyr Glu Asn Val
145                 150                 155                 160

Phe Thr Ala Tyr Cys Ala Ser Lys Thr Phe Ala Glu Lys Glu Ala Trp
                165                 170                 175

Lys Phe Val Lys Glu Asn Ser Asp Ala Val Lys Phe Lys Leu Thr Thr
                180                 185                 190

Ile His Pro Ser Phe Val Phe Gly Pro Gln Asn Phe Asp Glu Asp Val
            195                 200                 205

Thr Lys Lys Leu Asn Glu Thr Cys Glu Ile Ile Asn Gly Leu Leu His
            210                 215                 220

Ala Pro Phe Asp Thr Lys Val Glu Lys Thr His Phe Ser Gln Phe Ile
225                 230                 235                 240

Asp Val Arg Asp Val Ala Lys Thr His Val Leu Gly Phe Gln Lys Asp
                245                 250                 255

Glu Leu Ile Asn Gln Arg Leu Leu Leu Cys Asn Gly Ala Phe Ser Gln
                260                 265                 270

Gln Asp Ile Val Asn Val Phe Asn Glu Asp Phe Pro Glu Leu Lys Gly
            275                 280                 285

Gln Phe Pro Pro Glu Asp Lys Asp Thr Asp Leu Asn Lys Gly Val Thr
            290                 295                 300

Gly Cys Lys Ile Asp Asn Glu Lys Thr Lys Lys Leu Leu Ala Phe Glu
305                 310                 315                 320

Phe Thr Pro Phe His Lys Thr Ile His Asp Thr Val Tyr Gln Ile Leu
                325                 330                 335

His Lys Glu Gly Arg Val
            340

<210> SEQ ID NO 3
<211> LENGTH: 21
<212> TYPE: DNA
<213> ORGANISM: Artificial Sequence
<220> FEATURE:
<223> OTHER INFORMATION: Synthetic DNA

<400> SEQUENCE: 3
actatccacc cagttttcgt t                                              21

<210> SEQ ID NO 4
<211> LENGTH: 21
<212> TYPE: DNA
<213> ORGANISM: Artificial Sequence
<220> FEATURE:
<223> OTHER INFORMATION: Synthetic DNA

<400> SEQUENCE: 4
tccgaaaacg aaaactgggt g                                              21

<210> SEQ ID NO 5
<211> LENGTH: 21
<212> TYPE: DNA
<213> ORGANISM: Artificial Sequence
<220> FEATURE:
<223> OTHER INFORMATION: Synthetic DNA

<400> SEQUENCE: 5
```
actatccacc catggttcgt t    21

<210> SEQ ID NO 6
<211> LENGTH: 21
<212> TYPE: DNA
<213> ORGANISM: Artificial Sequence
<220> FEATURE:
<223> OTHER INFORMATION: Synthetic DNA

<400> SEQUENCE: 6
tccgaaaacg aaccatgggt g    21

<210> SEQ ID NO 7
<211> LENGTH: 21
<212> TYPE: DNA
<213> ORGANISM: Artificial Sequence
<220> FEATURE:
<223> OTHER INFORMATION: Synthetic DNA

<400> SEQUENCE: 7
actatccacc cacctttcgt t    21

<210> SEQ ID NO 8
<211> LENGTH: 21
<212> TYPE: DNA
<213> ORGANISM: Artificial Sequence
<220> FEATURE:
<223> OTHER INFORMATION: Synthetic DNA

<400> SEQUENCE: 8
tccgaaaacg aaaggtgggt g    21

<210> SEQ ID NO 9
<211> LENGTH: 21
<212> TYPE: DNA
<213> ORGANISM: Artificial Sequence
<220> FEATURE:
<223> OTHER INFORMATION: Synthetic DNA

<400> SEQUENCE: 9
actatccacc caggtttcgt t    21

<210> SEQ ID NO 10
<211> LENGTH: 21
<212> TYPE: DNA
<213> ORGANISM: Artificial Sequence
<220> FEATURE:
<223> OTHER INFORMATION: Synthetic DNA

<400> SEQUENCE: 10
tccgaaaacg aaacctgggt g    21

<210> SEQ ID NO 11
<211> LENGTH: 21
<212> TYPE: DNA
<213> ORGANISM: Artificial Sequence
<220> FEATURE:
<223> OTHER INFORMATION: Synthetic DNA

<400> SEQUENCE: 11
tatgaaaatg tcgttactgc t    21

<210> SEQ ID NO 12
<211> LENGTH: 21
<212> TYPE: DNA
<213> ORGANISM: Artificial Sequence

```
<220> FEATURE:
<223> OTHER INFORMATION: Synthetic DNA

<400> SEQUENCE: 12
acaataagca gtaacgacat t                                                    21
```

ALCOHOL DEHYDROGENASE MUTANT AND APPLICATION THEREOF IN SYNTHESIS OF DIARYL CHIRAL ALCOHOLS

TECHNICAL FIELD

The present disclosure relates to an alcohol dehydrogenase mutant and application thereof in synthesis of diaryl chiral alcohols, and belongs to the technical field of bioengineering.

BACKGROUND

Chiral diaryl alcohol compounds are key chiral intermediates for the synthesis of numerous drugs and fine chemicals, where chiral (4-chlorophenyl)-(pyridin-2-yl)-methanol (CPMA) is a key chiral intermediate for the synthesis of an antihistamine drug betahistine. The synthesis of chiral CPMA by chemical asymmetric reduction using prochiral (4-chlorophenyl)-(pyridin-2-yl)-methanone (CPMK) as a raw material is mainly achieved by the following five techniques:

1. at a substrate concentration of 1.0 mM, using trans-$RuCl_2[(R)$-xylbinap][(R)-daipen] as a catalyst to react at room temperature for 24 h under the nitrogen pressure of 40-60 psi, so as to obtain (S)-(4-chlorophenyl)-(pyridin-2-yl)-methanol ((S)-CPMA) with an ee value of 60.6% and a yield of 98% through reduction (C. Y. Chen, et al., Org. Lett., 2003, 5, 5039-5042);

2. using (S)-[Ru(BINAP)$Cl_2$]2($NE_3$) as a catalyst to obtain (S)-CPMA with an ee value of 99% through pressurization, hydrogenation and reduction (Zhao Zhiquan, et al., Chinese Journal of Pharmaceuticals, 2006, 37, 726-727);

3. using CPMK as a raw material and (S,S)-6-CHOONa as a catalyst to react at 50° C. and a substrate concentration of only 0.2 mM for 24 h, so as to obtain (R)-(4-chlorphenyl)-(pyridin-2-yl)-methanol ((R)-CPMA) with an ee value of 40.8% and a yield of 90% through reduction (B. G. Wang, Org. Lett., 2017, 19, 2094-2097);

4. using CPMK as a raw material for three-step reaction, (1) first protecting with trifluoromethanesulfonic anhydride and the like, (2) using a catalyst palladium ligand and Me-CBS to reduce a carbonyl group to an S configuration hydroxyl group, and (3) performing deprotection by triphenylphosphine palladium, so as to obtain (S)-CPMA (Chinese patent CN101848893A); and 5. using chiral BINAL-H as a chiral reducing agent for oriented synthesis of a single configuration of CPMA at a substrate concentration of 400 mM CMPK, where after recrystallization of ethyl acetate-petroleum ether, the yield of (R)-CPMA is 88.2%, the purity is 96.2%, the yield of (S)-CPMA is 87.4%, and the purity is 95.7% (Chinese patent CN103121966A).

It can be seen that the above reactions have the problems of high cost of the noble metal ligand catalysts, low substrate concentration, high pressure conditions for the reactions, many operation steps, and low optical purity of the materials, which cannot meet the requirements of drugs on the optical purity, and is not favorable for industrial production.

Biocatalysis refers to a process of chemical conversion using enzymes or biological organisms (cells, organelles, tissues, etc.) as a catalyst under mild action conditions, which is completed in an environment of normal temperature, a neutral environment, water or the like, and has unique advantages for the synthesis of chiral active pharmaceutical ingredients. It meets the goals of industrial development such as "sustainable development", "green chemistry" and "environmentally benign manufacturing". Compared with chemical synthesis methods, the use of alcohol dehydrogenase to asymmetrically reduce the carbonyl group in prochiral ketone has the advantages of high stereoselectivity, mild reaction conditions and the like, and has important economic and social values and ecological significance. The biological asymmetric reduction method may be realized mainly by the following four techniques:

1. in 2007, after Truppo et al. screened a series of commercial ketoreductases KRED, it was found that although some ketoreductases had a reducing ability to diaryl substrates, the stereoselectivity was just ordinary, a substrate spectrum was narrow, and substituent groups in the substrates had a great impact on the stereoselectivity; and only KRED124 may asymmetrically reduce CPMK to generate (R)-CPMA, the ee value was 94%, the conversion rate was 98%, and the addition of glucose dehydrogenase was required to achieve coenzyme circulation (M. D. Truppo, Org. Lett., 2007, 9, 335-338);

2. in 2009, Zhu Dunming et al. discovered that a recombinant carbonyl reductase SsCR derived from Sporobolomyces salmonicolor and mutants thereof may stereoselectively reduce different diaryl ketone substrates (8-99% ee), with the aid of glucose dehydrogenase, (R)-CPMA was generated by reducing CPMK, the conversion rate was 62%, and the enantioselectivity was 88% (R) (D. M. Zhu, Org. Lett., 2008, 10, 525-528);

3. in 2012, Zhou Jieyu et al. screened a Kluyveromyces sp. CCTCCM2011385 by traditional enrichment culture, which may catalyze the reduction of CPMK to generate (5)-CPMA (87% ee), however, due to the low content of active enzyme in wild fungi, only a 2 g/L substrate may be catalyzed at most, the product concentration is low, and the separation cost is high, so it cannot meet application needs, (Y. Ni, Process Biochem., 2012, 47, 1042-1048; Chinese patent CN102559520A); and 4. in 2013, Li Zhe et al. studied the asymmetric reduction to a series of diaryl ketones by a carbonyl reductase PasCR derived from Pichia pastoris GS115, the substrate concentration was 10 mM and the conversion rate was only 50% at most, (LiZhe, et al., Chinese Journal of Biotechnology, 2013, 29, 68-77).

It can be seen that the stereoselectivity for preparing chiral CPMA by the biological asymmetric reduction method can hardly meet the pharmaceutical requirement for an enantiomeric excess of more than 95%, and in particular, a reductase for synthesizing and preparing (S)-CPMA is unavailable, so there is an urgent need to develop a highly efficient and highly stereoselective bioenzyme catalyst.

SUMMARY

In view of the problem of low stereoselectivity of alcohol dehydrogenase in the prior art, the present disclosure provides a series of alcohol dehydrogenase mutant proteins, a nucleic acid sequence encoding the mutant proteins, a recombinant expression vector and a recombinant expression transformant containing the nucleic acid sequence, and the application of the alcohol dehydrogenase mutant proteins or the recombinant transformant expressing the alcohol dehydrogenase mutant proteins as a catalyst in asymmetric reduction and preparation of an optical chiral diaryl alcohol.

The present disclosure provides an alcohol dehydrogenase mutant with higher reactivity and stereoselectivity.

In an embodiment of the present disclosure, the amino acid sequence of the alcohol dehydrogenase mutant includes an amino acid sequence obtained by mutation of one or two amino acid sites of amino acid phenylalanine at position 161 and amino acid serine at position 196 in an amino acid sequence shown in SEQ ID No. 2.

In an embodiment of the present disclosure, the mutant includes the substitution of valine for serine at position 196 of the alcohol dehydrogenase with the amino acid sequence shown in SEQ ID No. 2, which is named M1.

In an embodiment of the present disclosure, the mutant includes the substitution of tryptophan for serine at position 196 of the alcohol dehydrogenase with the amino acid sequence shown in SEQ ID No. 2, which is named M2.

In an embodiment of the present disclosure, the mutant includes the substitution of proline for serine at position 196 of the alcohol dehydrogenase with the amino acid sequence shown in SEQ ID No. 2, which is named M3.

In an embodiment of the present disclosure, the mutant includes the substitution of glycine for serine at position 196 of the alcohol dehydrogenase with the amino acid sequence shown in SEQ ID No. 2, which is named M4.

In an embodiment of the present disclosure, the mutant includes the substitution of glycine for serine at position 196 of the alcohol dehydrogenase with the amino acid sequence shown in SEQ ID No. 2, and the substitution of valine for phenylalanine at position 161, which is named M5.

In an embodiment of the present disclosure, a recombinant strain expressing the mutant is provided.

In an embodiment of the present disclosure, a method for constructing the recombinant strain includes the following steps: cloning a nucleic acid molecule encoding the mutant into a recombinant vector, transforming the resulting recombinant vector into a transformant to obtain a recombinant expression transformant, and culturing the resulting recombinant expression transformant and conducting isolation and purification to obtain the mutant.

In an embodiment of the present disclosure, the host of the recombinant strain is *Escherichia coli*, and plasmid is pET28a (+).

In an embodiment of the present disclosure, the host of the recombinant strain is *E. coli* BL21 (DE3).

The present disclosure also provides a method for producing an alcohol dehydrogenase by using the recombinant strain, specifically including the following steps: inoculating the recombinant strain into an LB medium containing 40-60 μg/mL kanamycin sulfate for shake cultivation at 30-40° C. and 100-200 rpm, adding 0.05-1.0 mM isopropyl-β-D-thiogalactofuranoside (IPTG) for induction at an inducing temperature of 16-30° C. when the absorbance $OD_{600}$ of a medium solution reaches 0.5-1.0, and inducing for 5-10 h to obtain the mutant for efficient expression of the recombinant alcohol dehydrogenase.

In an embodiment of the present disclosure, application of the mutant as a catalyst in the preparation of an optical pure chiral diaryl alcohol by asymmetric reduction of a prochiral carbonyl compound is provided.

In an embodiment of the present disclosure, the prochiral carbonyl compound is (4-chlorophenyl)-(pyridin-2-yl)-methanone (CPMK), phenyl-(pyridin-2-yl)-methanone, (4-chlorophenyl)-(phenyl)-methanone, (4-fluorophenyl)-(phenyl)-methanone, (4-bromophenyl)-(phenyl)-methanone or (4-methoxyphenyl)-(phenyl)-methanone.

A method for producing chiral CPMA using an alcohol dehydrogenase specifically includes the following steps: constructing a reaction system, where CPMK concentration is 10-500 mM, the amount of the dehydrogenase mutant according to any one of claims 1-3 is 1-10 kU/L, and the amount of $NADP^+$ is 0.1-1.0 mM; adding a coenzyme circulation system, wherein the coenzyme circulation system contains glucose dehydrogenase GDH and D-glucose, the amount of glucose dehydrogenase GDH is 1-10 kU/L, and the amount of D-glucose dosage is 20-1000 mM, and the concentration of a phosphate buffer is 0.1-0.2 M; performing reaction at 30-35° C. and pH 6-8 for 1-24 h; and extracting the chiral CPMA from a reaction solution according to an organic solvent extraction method after asymmetric reduction reaction.

In an embodiment of the present disclosure, the coenzyme circulation system may also be phosphite/phosphite dehydrogenase (FTDH), formic acid/formate dehydrogenase (FDH), lactic acid/lactate dehydrogenase (LDH) or glycerol/glycerol dehydrogenase.

In an embodiment of the present disclosure, the (R)- and (S)-CPMA is chromatographed by taking 100 μL reaction solution, adding 500 μL ethyl acetate, shaking for 1-2 min, centrifuging at 12,000 rpm for 2-5 min, placing a supernatant into a centrifuge tube, and after an organic phase is naturally volatilized completely, adding 500 μL chromatographic pure ethanol for chiral liquid chromatography of a conversion rate and an ee value. The specific chromatographic conditions are as follows: Daicel Chiralcel OB—H (5 μm, 250 mm×4.6 mm) liquid chromatography column, mobile phases are n-hexane:ethanol:ethanolamine (90:10:0.01, v/v/v), the flow rate is I mL/min, the column temperature is 30° C., the UV detection wavelength is 254 nm, the injection volume is 10 μL, and the retention time for (S)-CPMA and that for (R)-CPMA are 11.14 min and 12.34 min respectively; (R)- and (S)-(4-fluorophenyl)-(phenyl)-methanol is chromatographed under the following conditions: Daicel Chiralcel OD-H (5 μm, 250 mm×4.6 mm) liquid chromatography column, mobile phases are n-hexane: ethanol:ethanolamine (90:10:0.01, v/v/v), the flow rate is I mL/min, the column temperature is 30° C., the UV detection wavelength is 254 nm, the injection volume is 10 μL, and the retention time for (S)-CPMA and that for (R)-CPMA are 6.29 min and 7.10 min respectively; and the (R)- and (S)-(4-methoxyphenyl)-(phenyl)-methanol is chromatographed under the following conditions: Daicel Chiralcel OD-H (5 μm, 250 mm×4.6 mm) liquid chromatography column, mobile phases are n-hexane:ethanol:ethanolamine (90:10:0.01, v/v/v), the flow rate is I mL/min, the column temperature is 30° C., the UV detection wavelength is 254 nm, the injection volume is 10 μL, and the retention time for (S)-CPMA and that for (R)-CPMA are 6.96 min and 8.45 min respectively.

The present disclosure has the beneficial effects that:

(1) the alcohol dehydrogenase mutant obtained in the present disclosure has high activity to various carbonyl compounds, and may catalyze the reduction of a plurality of aliphatic or aryl-substituted ketone substrates, especially diaryl ketone substrates having a large steric hindrance, and molecular modification on KpADH is achieved through the combination of mutation means to increase the stereoselectivity of the enzyme, which will make it more industrially useful;

(2) compared with the wild type alcohol dehydrogenase KpADH, the alcohol dehydrogenase mutants M1, M2 and M3 of the present disclosure have improved R-stereoselectivities for the substrate CPMK, and the ee value of the product CPMA is increased to 98.7% (M1), 97.7% (M2) and 95.2% (M3) from 82% (R) of the wild type; M4 has an R-stereoselectivity with an inverted trend for the substrate CPMK, and the ee value of the product CPMA is decreased to 27.2% from 82% (R) of the wild type; in addition, the M4 reduction substrate (4-fluorophenyl)-(phenyl)-methanone has an excellent stereoselectivity, the product configuration is the same as that of the wild type, and the ee value is 99.5%; M5 has an inverted S-stereoselection for the substrate CPMK, and the ee value of the mutant reduction product CPMA is 75.4% (S); in addition, the M5 reduction substrate (4-methoxyphenyl)-(phenyl)-methanone has an excellent stereoselectivity, the product configuration is the same as that of the wild type, and the ee value is 99.7%. The alcohol dehydrogenase mutant obtained in the present disclosure is particularly suitable for asymmetric reduction of diaryl ketones, and has good industrial application prospects.

DETAILED DESCRIPTION

Figure 1:
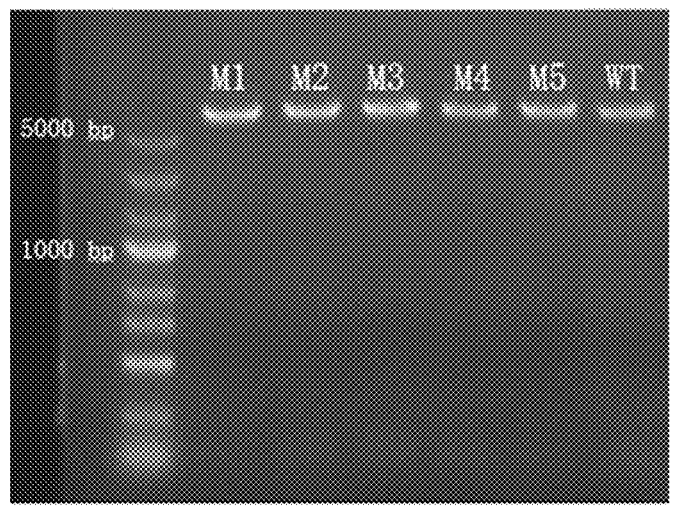
FIG. 1 is a whole plasmid PCR nucleic acid electrophoretogram of wild type and alcohol dehydrogenase mutants M1 to M5.
Figure 2:
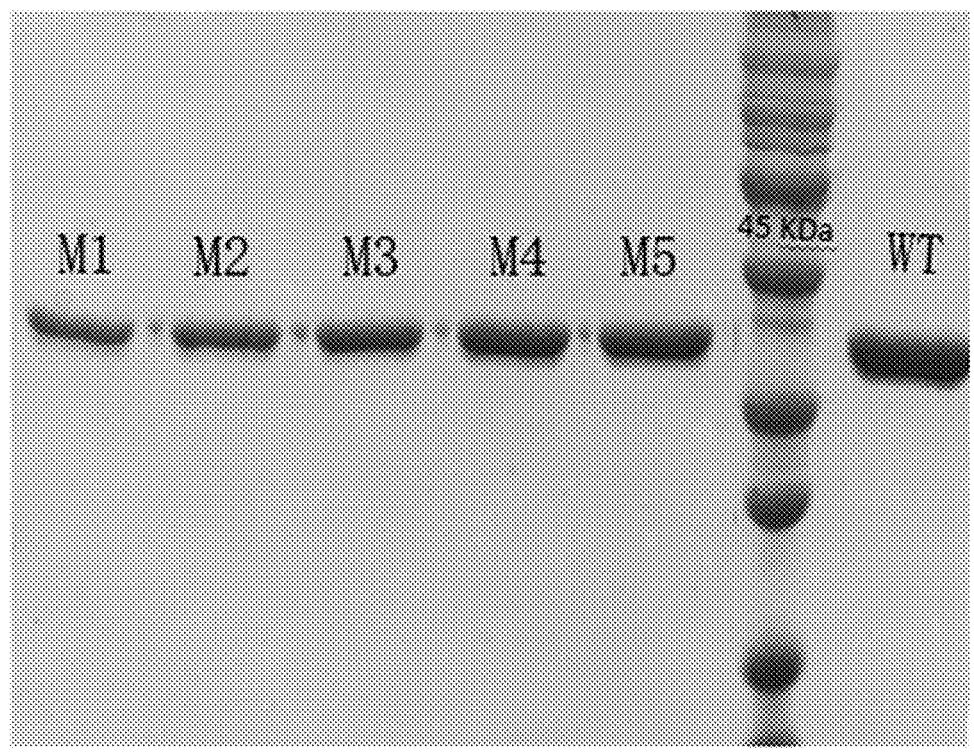
FIG. 2 is SDS-PAGE analysis of alcohol dehydrogenase mutants M1 to M5, respectively.
Figure 3:
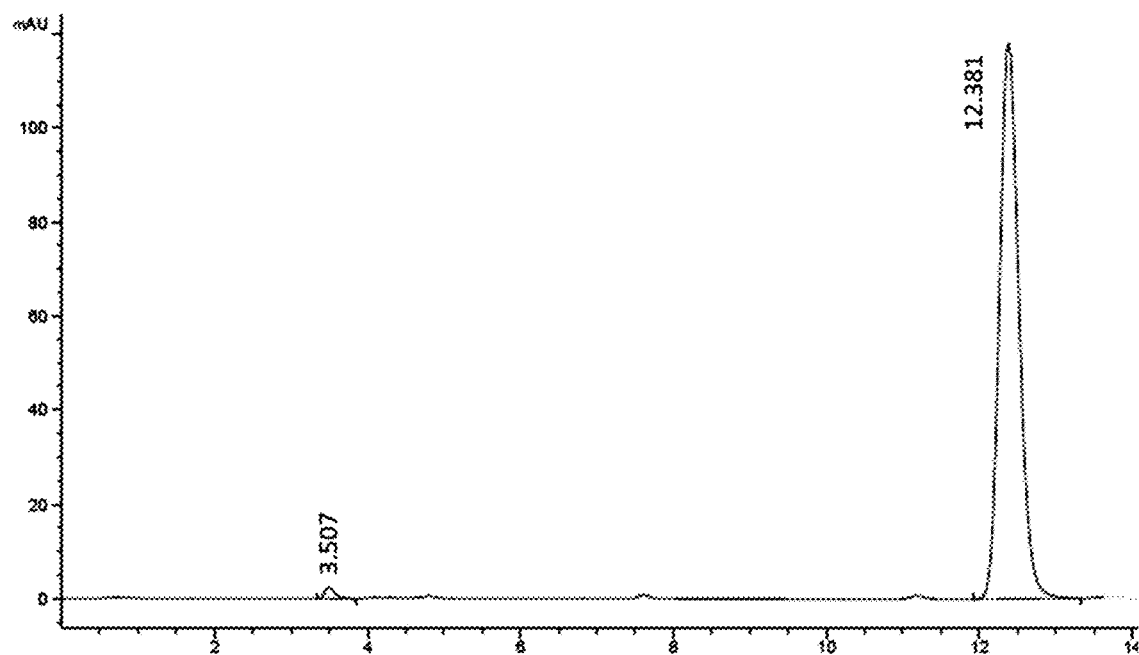
FIG. 3 is a chiral chromatogram of a product produced from CPMK reduction catalyzed by an alcohol dehydrogenase mutant M1.
Figure 4:
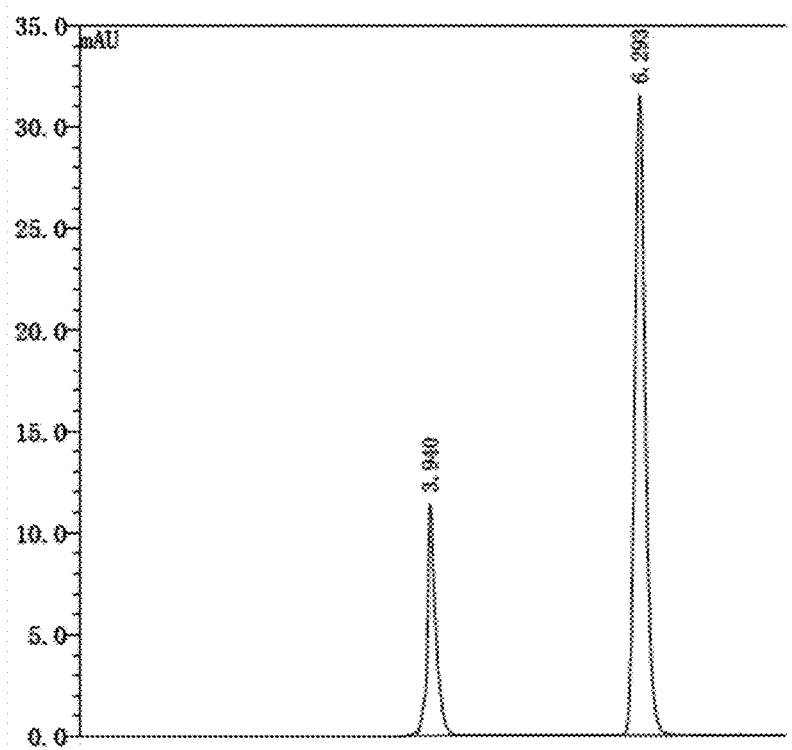
FIG. 4 is a chiral chromatogram of a product produced from (4-fluorophenyl)-(phenyl)-methanone reduction catalyzed by an alcohol dehydrogenase mutant M4.
Figure 5:
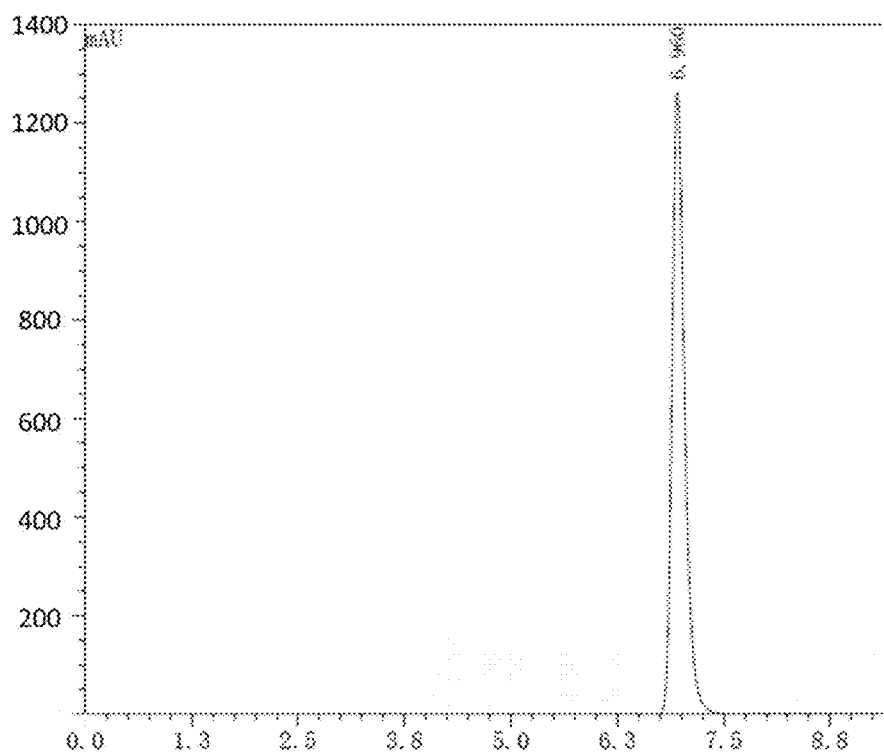
FIG. 5 is a chiral chromatogram of a product produced from (4-methoxy)-(phenyl)-methanone reduction catalyzed by an alcohol dehydrogenase mutant M5.

The present disclosure will be described in detail below by means of specific embodiments, but this does not limit the present disclosure to the scope of the described embodiments. The experimental methods without indicated specific experimental conditions in the following embodiments may be selected according to conventional methods and conditions, or according to the specification.

Example 1: Method for Measuring Activity of Alcohol Dehydrogenase and Optical Purity of Product Adopting a total reaction system of 200 μL, including: 1.0 mM NADPH, 1.0 mM substrate CPMK and sodium phosphate buffer (PBS, 100 mM, pH 7.0), fully and evenly mixing, maintaining at 30° C. for 2 min, adding an appropriate amount of enzyme solution, and detecting the change in light absorption at 340 nm.

The enzyme activity was calculated by the following formula:

Enzyme activity (U)=EW×V×10³/(6220×1);

in the formula, EW is the change in absorbance at 340 nm in 1 min; V is the volume of a reaction solution in mL; 6220 is the molar extinction coefficient of NADPH in L/(mol·cm); and 1 is the optical path distance in cm. One activity unit (U) corresponds to the amount of enzyme required to catalyze the oxidation of 1 μmol NADPH per minute under the above conditions.

Method for determining optical purity ee:

$$ee = \frac{AS - AR}{AS + AR} \times 100\%;$$

As: molar concentration of (S)-CPMA obtained by liquid chromatography; and $A_R$: molar concentration of (R)-CPMA obtained by liquid chromatography.

Example 2: Construction of Alcohol Dehydrogenase Mutant Gene and Recombinant Expression Transformant A whole plasmid PCR method was used for site-directed mutagenesis on amino acid residues at positions 161 and 196 to construct an iterative combination mutant. The primer design was as follows (all described in the 5'-3' direction, and the underline represents the mutation site):

```
M1 (using pET28a-KpADH recombinant plasmid as a
template):
S196V-F:   ACTATCCACCCAGTTTTCGTT;   (SEQ ID No. 3)

S196V-R:   TCCGAAAACGAAAACTGGGTG;   (SEQ ID No. 4)

M2 (using pET28a-KpADH recombinant plasmid as a
template):
S196W-F:   ACTATCCACCCATGGTTCGTT;   (SEQ ID No. 5)

S196W-R:   TCCGAAAACGAACCATGGGTG;   (SEQ ID No. 6)

M3 (using pET28a-KpADH recombinant plasmid as a
template):
S196P-F:   ACTATCCACCCACCTTTCGTT;   (SEQ ID No. 7)

S196P-R:   TCCGAAAACGAAAGGTGGGTG;   (SEQ ID No. 8)

M4 (using pET28a-KpADH recombinant plasmid as a
template):
S196G-F:   ACTATCCACCCAGGTTTCGTT;   (SEQ ID No. 9)

S196G-R:   TCCGAAAACGAAACCTGGGTG;   (SEQ ID No. 10)

M5 (using M4 recombinant plasmid as a template):
F161V-F:   TATGAAAATGTCGTTACTGCT;   (SEQ ID No. 11)

F161V-R:   ACAATAAGCAGTAACGACATT.   (SEQ ID No. 12)
```

A PCR reaction system was: a PCR reaction system (50 μL) including KOD enzyme (2.5 U/mL) 1.0 μL, template (5-50 ng) 1.0 μL, dNTP 4.0 μL, 10× reaction buffer 5.0 μL, forward primer 1.0 μL, reverse primer 1.0 μL, and the rest of ddH2O to make the reaction system 50 μL in total.

A PCR amplification procedure was: (1) denaturation at 94° C. for 3 min, (2) denaturation at 94° C. for 30 sec, (3) annealing at 54° C. for 30 sec, (4) extension at 72° C. for 150 sec, repeating steps (2) to (4) for 10-15 cycles, finally extension at 72° C. for 10 min, and storing a PCR amplification product at 4° C.

After PCR, Dpnl restriction enzyme was added into a reaction mixture and incubated at 37° C. for 1 h, 10 μL digested PCR reaction solution was transferred into 50 μL *E. coli* BL21 (DE3) competent cells through CaCl₂ thermal transformation, and the cells were used to uniformly coat an LB agar plate containing 50 μg/mL kanamycin sulfate for inversion culture at 37° C. for 12 h.

Example 3: Expression and Purification of Alcohol Dehydrogenase and Mutant Thereof Recombinant *Escherichia coli* carrying a stereoselective improvement mutant was inoculated into an LB medium containing kanamycin sulfate (50 μg/mL) at a transfer amount of 2% for shake cultivation at 37° C. and 200 rpm, 0.2 mM isopropyl-β-D-thiogalactofuranoside (IPTG) was added for induction at 25° C. when the absorbance OD₆₀₀ of the medium reached 0.8, after 8 hours of induction, a strain for efficient expression of a recombinant alcohol dehydrogenase mutant was obtained through 10 minutes of centrifugation at 8000 rpm, and the collected strain was suspended in a potassium phosphate buffer (100 mM, pH 6.0) for ultrasonication.

A column used for purification was a nickel affinity column HisTrap FF crude, and purification was achieved through affinity chromatography using a histidine tag on recombinant protein. The nickel column was equilibrated with a solution A first, a crude enzyme solution was loaded, a penetrating peak was further eluted off using the solution A, and after equilibrium, a solution B (20 mM sodium phosphate, 500 mM NaCl, and 1000 mM imidazole, pH 7.4) was used for gradient elution to elute off the recombinant protein bound to the nickel column, so as to obtain the recombinant alcohol dehydrogenase mutant. The purified protein was subjected to activity measurement (CPMK as substrate, and NADPH as coenzyme) and SDS-PAGE analysis. After purification of the nickel column, a single band was displayed at around 45 kDa, and the amount of impure protein was small, indicating that the column purification effect was good. The purified alcohol dehydrogenase protein was then replaced into a Tris-HCl (100 mM, pH 7.0) buffer using a Hi Trap Desalting column (GE Healthcare).

Example 4: Kinetic and Stereoselective Analysis of Alcohol Dehydrogenase Mutant

The activity of KpADH at different substrate concentrations and coenzyme concentrations was determined, and a double reciprocal curve was made based on the reciprocal of activity and substrate concentration to calculate kinetic parameters.

It can be seen from Table 1 that the $k_{cat}/K_m$ of KpADH to CPMK was 28.9 $s^{-1} \cdot mM^{-1}$, the reduction product configuration was R configuration, and the ee value was 82.5%. The stereoselectivity of (R)-CPMA synthesized by mutants M1, M2 and M3 was increased to 95% or above, and the ee values of the products were 98.7%, 97.7% and 95.2% respectively. Mutant M4 showed a reduced stereoselectivity, the reduction product configuration was also R configuration, and the ee value of the product was 22.4%. Mutant M5 showed an inverted stereoselectivity, the reduction product was in the S configuration, and the ee value of the product was 75.4%.

TABLE 1

Kinetic parameters and stereoselectivity of alcohol dehydrogenase mutant

| Enzyme | Km (mM) | Vmax (μmol · min$^{-1}$ · mg$^{-1}$) | Kcat (s$^{-1}$) | Kcat/Km (s$^{-1}$ · mM$^{-1}$) | ee (%) | Config. (R/S) |
|---|---|---|---|---|---|---|
| KpADH | 0.410 | 17.9 | 11.8 | 28.9 | 82.5 | R |
| M1 | 0.72 | 21.3 | 17.0 | 23.6 | 98.7 | R |
| M2 | 0.702 | 21.3 | 14.2 | 20.3 | 97.7 | R |
| M3 | 0.604 | 22.3 | 14.8 | 24.6 | 95.2 | R |
| M4 | 0.730 | 26.5 | 17.6 | 24.1 | 22.3 | R |
| M5 | 0.69 | 17.69 | 11.79 | 17.09 | 75.4 | S |

Example 5: Substrate Specificity Analysis of Alcohol Dehydrogenase Mutant

The reduction of prochiral carbonyl compounds by the alcohol dehydrogenase mutant obtained in Embodiment 2 was studied, and the studied prochiral carbonyl compounds include (4-chlorophenyl)-(pyridin-2-yl)-methanone (CPMK), phenyl-(pyridin-2-yl)-methanone, (4-chlorophenyl)-(phenyl)-methanone, (4-fluorophenyl)-(phenyl)-methanone, (4-brormophenyl)-(phenyl)-methanone and (4-methoxyphenyl)-(phenyl)-methanone. It can be seen from Table 2 that for the substrate CPMK, the reduction products of M1, M2 and M3 were all in the R-configuration, and the ee values of the products were all higher than 95%; for the substrate phenyl-pyridin-2-yl-ketone, only the ee value of the reduction product of M3 was 95% or above, and the configuration of the reduction product of M5 was opposite to that of the female parent, with the value of 75.5%. For the substrate (4-bromophenyl)-(pyridin-2-yl)-methanone, the ee value of the catalytic product of M1 was 99% or above, and the ee value of the catalytic product of M2 was also high, which was 95.5%; and for (4-fluorophenyl)-(pyridin-2-yl)-methanone and (4-methoxyphenyl)-(phenyl)-methanone, the ee value of each catalytic product of M5 was 95% or above, and the configuration was identical to that of the female parent.

TABLE 2

Substrate specificity of alcohol dehydrogenase mutant

| Substrate | WT | M1 | M2 | M3 | M4 | M5 |
|---|---|---|---|---|---|---|
| 4-Cl-C6H4-CO-pyridin-2-yl | 81.9 (R) | 99.7 (R) | 97.7 (R) | 95.2 (R) | 22.3 (R) | 75.4 (S) |
| C6H5-CO-pyridin-2-yl | 26.3 (R) | 71.0 (R) | 80.6 (R) | 96.5 (R) | 20.7 (R) | 75.5 (S) |
| 4-Cl-C6H4-CO-C6H5 | 71.4 (S) | 93.2 (S) | 97.9 (S) | 93.2 (S) | 38.6 (R) | 62.0 (R) |
| 4-Br-C6H4-CO-C6H5 | 69.2 (S) | 99.3 (S) | 95.5 (S) | 63.3 (R) | 66.5 (R) | 70.9 (R) |
| 4-F-C6H4-CO-C6H5 | 25.3 (R) | 57.51 (R) | 65.6 (R) | 45.6 (R) | 99.5 (R) | 96.5 (R) |
| 4-CH3O-C6H4-CO-C6H5 | 14.9 (R) | 42.7 (R) | 53.2 (R) | 50.6 (R) | 82.6 (R) | 99.7 (R) |

Example 6: Preparation of (R)-CPMA with High Optical Purity Through Asymmetric Reduction of CPMK by Alcohol Dehydrogenase Mutant A 20 mL biocatalytic system was established: 100 mM potassium phosphate buffer (pH 7.0), and the alcohol dehydrogenase mutant M1 obtained in Embodiment 2 as well as wild KpADH 10 g/L, CPMK 100 mM, 200 mM and 500 mM were added (substrate added in batches). The reaction was performed at 30° C. and 200 rpm for 12 h with a constant pH of 7.5. The conversion rate analysis results during the reaction are shown in Table 3 and Table 4. It can be seen that both the wild type dehydrogenase and the mutant M1 may asymmetrically reduce 100 mM and 200 mM CPMK. When the CPMK concentration was 200 mM, the wild type KpADH and the mutant M1 required 12 h and 24 h respectively to achieve a conversion rate close to 99.9%. The final reduction product of the wild type KpADH was (R)-CPMA, and the ee value was 82%; and the final reduction product of the mutant M1 was also (R)-CPMA, and the ee value was 99.7%. The obtained crude products of (R)-CPMA were redissolved in ethanol, and corresponding pure products of (R)-CPMA were added as seed crystals to recrystallize at 4° C. to finally obtain products with optical purity greater than 99.9% ee.

TABLE 3

Asymmetric reduction of CPMK catalyzed by wild type alcohol dehydrogenase KpADH

| Reaction time (h) | Conversion rate (%) | | |
|---|---|---|---|
| | 100 mM | 200 mM | 500 mM |
| 1 | 47.76 | 25.6 | 11.7 |
| 2 | 77.9 | 36.9 | 20.1 |
| 3 | 87.1 | 50.5 | 44.8 |
| 4 | 96.5 | 62.8 | 59.6 |
| 6 | 98.7 | 85.3 | 80.2 |
| 8 | 99.6 | 97.4 | 93.2 |
| 12 | >99.9 | 99.4 | 95.6 |
| 24 | >99.9 | 99.7 | 99.2 |

TABLE 4

Asymmetric reduction of CPMK catalyzed by alcohol dehydrogenase mutant M1

| Reaction time (h) | Conversion rate (%) | | |
|---|---|---|---|
| | 100 mM | 200 mM | 500 mM |
| 1 | 35.6 | 29.1 | 18.8 |
| 2 | 64.6 | 36.4 | 24.1 |
| 3 | 79.4 | 42.8 | 30.6 |
| 4 | 90.2 | 80.6 | 55.3 |
| 6 | 98.2 | 89.7 | 76.9 |
| 8 | 99.2 | 94.2 | 87.6 |
| 12 | 99.4 | 97.4 | 92.2 |
| 24 | 99.6 | 99.2 | 99.5 |

Example 7: Preparation of (R)-4-Fluorophenyl-Phenylmethanol with High Optical Purity Through Asymmetric Reduction of CPMK by Alcohol Dehydrogenase Mutant A 20 mL biocatalytic system was established: 100 mM potassium phosphate buffer (pH 7.0), and 10 g/L alcohol dehydrogenase mutant M4 cells obtained in Embodiment 2 and (4-fluorophenyl)-phenyl-methanone 50 mM were added. The reaction was performed at 30° C. and 200 rpm for 24 h with a constant pH of 7.5. The conversion rate analysis results during the reaction are shown in Table 5. When the substrate concentration was 50 mM, the alcohol dehydrogenase mutant M4 may achieve a substrate conversion rate of 99% or above within 24 h, and the reduction products were all (R)-4-fluorophenyl-phenylmethanol, wherein the ee value of the wild type KpADH reduction product was only 25.3%, and the ee value of the mutant M4 reduction product may reach 99.5%. The obtained crude products of (R)-4-fluorophenyl-phenylmethanol were redissolved in ethanol, and corresponding pure products were added as seed crystals to recrystallize at 4° C. to finally obtain products with optical purity greater than 99.9% ee.

TABLE 5

Asymmetric reduction of 50 mM (4-fluorophenyl)-phenyl-methanone catalyzed by alcohol dehydrogenase mutant M4

| Reaction time (h) | Conversion rate (%) | |
|---|---|---|
| | WT | M4 |
| 1 | 15.6 | 10.1 |
| 2 | 34.6 | 26.4 |
| 3 | 49.4 | 32.8 |
| 4 | 60.2 | 51.6 |
| 6 | 88.2 | 72.7 |
| 8 | 94.2 | 84.2 |
| 12 | 98.4 | 92.4 |
| 24 | 99.6 | 99.4 |

Example 8: Preparation of (R)-(4-methoxyphenyl)-(phenyl)-methanone with High Optical Purity Through Asymmetric Reduction of CPMK by Alcohol Dehydrogenase Mutant A 20 mL biocatalytic system was established: 100 mM potassium phosphate buffer (pH 7.0), and 10 g/L alcohol dehydrogenase mutant M4 cells obtained in Embodiment 2 and (4-methoxyphenyl)-(phenyl)-methanone were added. The reaction was performed at 30° C. and 200 rpm for 24 h with a constant pH of 7.5. The conversion rate analysis results during the reaction are shown in Table 6. When the substrate concentration was 50 mM, the alcohol dehydrogenase mutant M4 may achieve a substrate conversion rate of 99% or above within 24 h, and the reduction products were all (R)-4-methoxyphenyl-phenylmethanol, wherein the ee value of the wild type KpADH reduction product was only 15.1%, and the ee value of the mutant M4 reduction product may reach 99.7%. The obtained crude products of (R)-4-methoxyphenyl-phenylmethanol were redissolved in ethanol, and the corresponding pure products were added as seed crystals to recrystallize at 4° C. to finally obtain products with optical purity greater than 99.9% ee.

TABLE 6

Asymmetric reduction of CPMK catalyzed by alcohol dehydrogenase mutant M5

| Reaction time (h) | Conversion rate (%) | |
|---|---|---|
| | WT | M5 |
| 1 | 23.6 | 12.4 |
| 2 | 34.2 | 23.3 |
| 3 | 44.9 | 39.4 |
| 4 | 64.6 | 50.7 |
| 6 | 79.2 | 68.9 |
| 8 | 90.4 | 79.2 |
| 12 | 96.3 | 93.4 |
| 24 | 99.8 | 99.6 |

What is claimed is:

1. An alcohol dehydrogenase mutant, wherein the alcohol dehydrogenase mutant comprises an amino acid sequence having all of SEQ ID NO: 2 except for:
 (a) a substitution of valine for serine at position 196 of SEQ ID NO:2;
 (b) a substitution of glycine for serine at position 196 of SEQ ID NO:2;
 (c) a substitution of tryptophan for serine at position 196 of SEQ ID NO:2;
 (d) a substitution of proline for serine at position 196 of SEQ ID NO:2; or
 (e) a substitution of valine for phenylalanine at position 161 of SEQ ID NO:2 and a substitution of glycine for serine at position 196 of SEQ ID NO:2; and
 wherein the alcohol dehydrogenase mutant has alcohol dehydrogenase activity.

2. A method for producing chiral SE chlorophenyl)-(pyridin-2-yl)-methanol (CPMA) which comprises:
 combining the alcohol dehydrogenase mutant of claim 1 at a concentration of 1 to 10 kU/L with prochiral (4-chlorophenyl)-(pyridin-2-yl)-methanone (CPMK) at a concentration of 10 to 500 mM, and $NADP^+$ at a concentration of 0.1 to 1.0 mM;
 adding a coenzyme circulation system comprising glucose dehydrogenase at a concentration of 1 to 10 kU/L, D-glucose at a concentration of 20 to 1000 mM, and a phosphate buffer;
 incubating the coenzyme circulation system with the alcohol dehydrogenase mutant, CPMK, and $NADP^+$ at 30 to 35° C. and a pH of 6 to 8 for 1 to 24 hours to produce CPMA; and
 extracting the CPMA by adding an organic solvent after an asymmetric reduction reaction;
 wherein the coenzyme circulation system further comprises: (i) phosphite and phosphite dehydrogenase (FTDH), (ii) formic acid and formate dehydrogenase (FDH), (iii) lactic acid and lactate dehydrogenase (LDH), or (iv) glycerol and glycerol dehydrogenase.

* * * * *